US012491116B2

(12) United States Patent
Oliver et al.

(10) Patent No.: US 12,491,116 B2
(45) Date of Patent: Dec. 9, 2025

(54) SLEEP MASK PRODUCTS

(71) Applicant: THE INACTIVE COMPANY, LLC, Atlanta, GA (US)

(72) Inventors: Lori Oliver, Atlanta, GA (US); Lauren Rials, Atlanta, GA (US); Mayur Vansia, Atlanta, GA (US)

(73) Assignee: THE INACTIVE COMPANY, LLC, Atlanta, GA (US)

( * ) Notice: Subject to any disclaimer, the term of this patent is extended or adjusted under 35 U.S.C. 154(b) by 112 days.

(21) Appl. No.: 18/286,214

(22) PCT Filed: Apr. 7, 2022

(86) PCT No.: PCT/US2022/023896
§ 371 (c)(1),
(2) Date: Oct. 9, 2023

(87) PCT Pub. No.: WO2022/216972
PCT Pub. Date: Oct. 13, 2022

(65) Prior Publication Data

US 2024/0115424 A1 Apr. 11, 2024

Related U.S. Application Data

(60) Provisional application No. 63/171,939, filed on Apr. 7, 2021.

(51) Int. Cl.
*A61F 9/04* (2006.01)

(52) U.S. Cl.
CPC .................................... *A61F 9/04* (2013.01)

(58) Field of Classification Search
CPC .... A61F 9/04; A61F 9/045; A61F 9/06; A61F 9/02; A42B 1/018; A42B 1/0181
See application file for complete search history.

(56) References Cited

U.S. PATENT DOCUMENTS 7,135,424 B2 11/2006 Worley et al.
8,333,793 B2 12/2012 Igaki et al.
(Continued)

FOREIGN PATENT DOCUMENTS

CN 101133992 B * 12/2010
CN 106726131 A * 5/2017 .............. A61N 5/06
(Continued)

OTHER PUBLICATIONS

The Inactive Company, Inactivators—The First Performance Sleep Mask, Oct. 10, 2021 [retrieved on Jun. 12, 2022]. Retrieved from the internet: <URL: https://inactiveco.com/shop/>, entire document.

*Primary Examiner* — Tarla R Patel
(74) *Attorney, Agent, or Firm* — Brown Rudnick LLP; Richard T. Timmer

(57) ABSTRACT

The present disclosure relates to sleep mask products and methods of making same. Disclosed are sleep mask products comprising: a mask body and a mask strap; wherein the mask strap has a first attachment point to a first lateral edge of the mask body and a second attachment point to a second lateral edge of the mask body; and wherein the mask body comprises a first fabric layer; a second fabric layer; a first foam layer; and a second foam layer. The second fabric inner surface comprises a phase change material thereon. The second foam layer second surface contacts the phase change material, the second fabric inner surface, or a combination thereof. This abstract is intended as a scanning tool for purposes of searching in the particular art and is not intended to be limiting of the present disclosure.

17 Claims, 9 Drawing Sheets

(56) References Cited

U.S. PATENT DOCUMENTS

| | | | |
|---|---|---|---|
| 10,667,951 | B2 | 6/2020 | Renaud |
| 2010/0122398 | A1 | 5/2010 | Luciano |
| 2013/0273365 | A1 | 10/2013 | Hartmann et al. |
| 2014/0331383 | A1 | 11/2014 | Bially |
| 2017/0361048 | A1 | 12/2017 | Moiler et al. |
| 2019/0159929 | A1 | 5/2019 | Bruder |

FOREIGN PATENT DOCUMENTS

| | | | | | |
|---|---|---|---|---|---|
| DE | 102016113705 | B3 | * | 12/2017 | ............... A61F 9/04 |
| GB | 2561707 | A | | 10/2018 | |
| JP | 3142860 | U | | 6/2008 | |
| KR | 10-2012-0130841 | A | | 12/2012 | |
| WO | 2016/176175 | A1 | | 11/2016 | |

* cited by examiner

SLEEP MASK PRODUCTS

CROSS-REFERENCE TO RELATED APPLICATIONS

This application is the 35 U.S.C. § 371 national stage application of PCT Application No. PCT/US2022/023896, filed Apr. 7, 2022, where the PCT claims priority to, and the benefit of U.S. provisional application entitled "SLEEP MASK PRODUCTS" having Ser. No. 63/171,939, filed Apr. 7, 2021, both of which are herein incorporated by reference in their entireties.

BACKGROUND

In the United States, studies have documented that 1 in 3 adults do not get 7-9 hours of sleep per night which is generally considered the minimal sufficient hours of sleep for adults. The inability of many citizens to get sufficient sleep has been shown to result in about $400 billion loss in economic productivity. Moreover, it is estimated that about 60 million Americans have a chronic sleep disorder, and that sleep disorders are associated with about $16 billion of additional healthcare costs.

The health benefits of not only sufficient sleep, but high-quality sleep, are well documented and include increased concentration and productivity, an increase of about 60% in long term memory, an improvement of about 60% in performance of normal daily activities, at least a 4% improvement in reaction time, and healthier immune and cardiovascular systems.

The most significant outer contributor to insufficient and poor-quality sleep is light. Beyond the intuitive connection between light and sleep that most adults have, sleep research has determined that light plays a central role in regulating circadian rhythm, the body's inner clock that signals when to be alert and when to rest. Moreover, light also affects the production of melatonin, an essential sleep-promoting hormone. However, in many circumstances, it is not possible to sufficiently darken a room or local environment, e.g., at home, during travel or in a hotel room, to block out sufficient light to provide for high quality sleep.

Sleep masks to cover the eyes and block out any stray or incident light have been described. Critical to the compliant and regular use of a sleep mask is that it block essentially all incident light, is easy to adjust for individual fit, and provides for user comfort, including minimal localized heating. Currently available sleep mask products are often flat and lacking any components or structure to provide an ergonomic fit to a user's face. In addition, previously described sleep mask products are often either thin and lacking a robust, durable structure or are constructed with thick, bulky materials that provide for a poor-quality user experience. Importantly, previously described sleep mask products lack any integrated ability to cool or dissipate heat, and frequently create a heat trap or sink around or beneath the mask structure. However, perhaps due to deficiencies with currently available sleep mask designs, only about 10% of the population has even tried sleep masks.

Despite a variety of conventional products that purport to provide an optimal sleep mask experience, the currently available solutions suffer a deficiency in one or more of these key criteria as described above, as well as provide an optimal experience at a reasonable cost point. These needs and other needs are satisfied by the present disclosure.

SUMMARY

In accordance with the purpose(s) of the disclosure, as embodied and broadly described herein, the disclosure, in one aspect, relates to sleep mask products and methods of making same. In various aspects, disclosed herein are sleep mask products comprising a layered foam structure comprising at least one ergonomically molded foam layer, e.g., a soft foam layer, that provides a low-profile and non-bulky user experience. Moreover, the disclosed sleep mask products comprise a phase change material (PCM) and thereby provide a sleep mask product with an integrated cooling component.

Disclosed herein are sleep mask products comprising: a mask body and a mask strap; wherein the mask strap has a first attachment point to a first lateral edge of the mask body and a second attachment point to a second lateral edge of the mask body; wherein an inner surface of the mask body together with an inner surface of the mask strap can form an annulus configured to allow placement of the mask body on a face of a human subject and placement of the mask strap around lateral and anterior portions of a head of the human subject; wherein the mask body comprises a first fabric layer; a second fabric layer; a first foam layer; and a second foam layer; wherein the first fabric layer has a first fabric outer surface and a first fabric inner surface; wherein the second fabric layer has a second fabric outer surface and a second fabric inner surface; wherein the first foam layer has a first foam layer first surface and a first foam layer second surface; wherein the second foam layer has a second foam layer first surface and a second foam layer second surface; wherein the first fabric inner surface contacts the first foam layer first surface; wherein the first foam layer second surface contacts the second foam layer first surface; wherein the second fabric inner surface comprises a phase change material thereon; wherein the second foam layer second surface contacts the phase change material, the second fabric inner surface, or a combination thereof; wherein the mask body has a first eye masking area, a second eye masking area, and a nose area; wherein the first eye masking area is configured to cover a first eye of the human subject and mitigate passage of light to the first eye; wherein the second eye masking area is configured to cover a second eye of the human subject and mitigate passage of light to the second eye; wherein the mask body has a mask body upper edge that is configured to be in contact with a portion of the brow or forehead when wore by the human subject; wherein the nose area is configured to fit over a nose of the human subject; wherein a brow fitting component is positioned parallel to the mask body upper edge and between the first foam layer second surface and the second foam layer first surface; and wherein nose fitting component is positioned parallel to the nose area edge and between the first foam layer second surface and the second foam layer first surface.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE FIGURES

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A shows a perspective front plan view with shading to accentuate relief perspective. This front view is of an outer surface that would be facing outward from a face of a human subject when positioned thereon. The view is of a sleep mask body without straps shown. FIG. 1B is a photographic image of a representative example of a front view of mask similar to that shown in FIG. 1A. FIG. 1C shows a perspective rear plan view with shading to accentuate relief perspective. This rear view is of an inner surface that would be facing inward towards a face of a human subject when positioned thereon and in at least partial contact therewith. The view is of a sleep mask body without straps shown. FIG. 1D is a photographic image of a representative example of a rear view of mask similar to that shown in FIG. 1C.

FIG. 2A shows a front plan view of a representative sleep mask product with positioning of a brow fitting component and a nose fitting, with index line a shown marking the position of the cross-sectional view depicted FIG. 2B. FIG. 2B shows a cross-sectional view taken at the position of the index line shown in FIG. 2A. FIG. 2C shows a photographic image of a cross-sectional portion of a disclosed sleep mask at a position similar to that shown in the drawing of FIG. 2B. FIG. 2D shows a portion of the cross-sectional view in order to delineate the relation of the features as disclosed herein. All reference characters have the meaning as given in Table 1 herein below.

FIG. 3A shows a front plan view of a representative sleep mask product with positioning of a brow fitting component and a nose fitting, with index line b shown marking the position of the cross-sectional view depicted FIG. 3B. FIG. 3B shows a cross-sectional view taken at the position of the index line shown in FIG. 3A. FIG. 3C shows a photographic image of a cross-sectional portion of a disclosed sleep mask at a position similar to that shown in the drawing of FIG. 3B. All reference characters have the meaning as given in Table 1 herein below.

FIG. 4A shows a representative cross-sectional side view of a second fabric layer having thereon a phase change coating on a second fabric inner surface such that the phase change coating is a discontinuous patterned coating. FIG. 4B shows a representative plan view of a second fabric layer inner surface having a phase change coating thereon such that the phase change coating forms a discontinuous patterned coating having a regular pattern. FIG. 4C shows a representative plan view of a second fabric layer outer surface having a phase change coating on the second fabric inner surface such that the phase change coating forms a discontinuous patterned coating having a regular pattern. FIG. 4D shows a photographic image of a representative plan view of a second fabric layer outer surface similar in context to the drawing of FIG. 4C. FIG. 4E shows a photographic image of a representative plan view of a second fabric layer inner surface similar in context to the drawing of FIG. 4B. It should be noted that photographic images shown in FIGS. 4D-4E are of a second fabric layer before fabrication into a disclosed sleep mask product. FIG. 4F shows a photographic image of a representative plan view of a second fabric layer inner surface fabricated as part of a disclosed sleep mask product. The photographic image is of the region corresponding to a first eye area and a portion of the nose area.

FIG. 7A shows a representative schematic depiction of a disclosed sleep mask strap formed from two bonded elastic pieces to provide the depicted side straps. FIG. 7B shows a representative schematic depiction of a disclosed sleep mask strap formed from two strap components that are stitched together as depicted in the figure. The strap configuration, also including the opening of the two elastic pieces around the back of the head, allows for maximum adjustment and hold for the wearer to achieve optimal personal fit and comfort, without the interference of metal or Velcro sizers to impede the sleep experience.

Figure 1B:
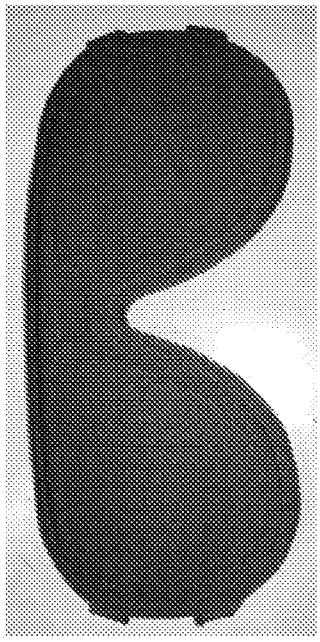
FIGS. 1A-1D show representative depictions of a disclosed sleep mask product.
Figure 1D:
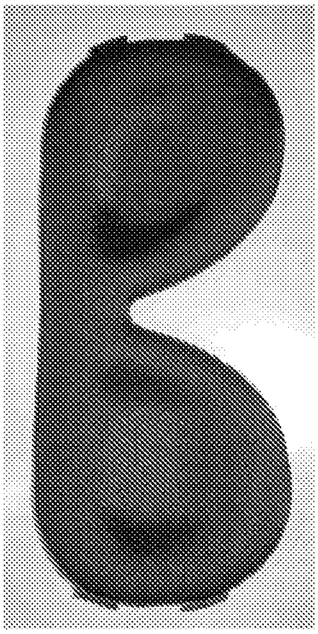
Figure 1A:
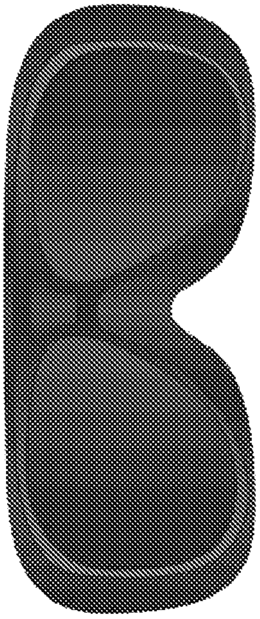
Figure 1C:
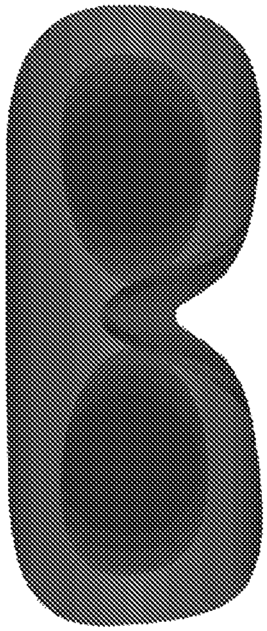

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

A. Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used herein, the term "and/or" includes any and all combinations of one or more of the associated listed items. Expressions such as "at least one of," when preceding a list of elements, modify the entire list of elements and do not modify the individual elements of the list.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item.

In the drawings, the size and relative sizes of layers and regions may be exaggerated for clarity.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

Reference to "a" phase change material refers to one or more molecules of the phase change material rather than being limited to a single molecule of the chemical compound. Furthermore, the one or more molecules may or may not be identical, so long as they fall under the category of the chemical compound. Thus, for example, "a" phase change material is interpreted to include one or more molecules of the phase change material, where the molecules may or may not be identical (e.g., molecular weight or chain length, isomeric variants, etc.).

As used in the specification and the appended claims, the singular forms "a," "an" and "the" include plural referents unless the context clearly dictates otherwise. Thus, for example, reference to "a phase change material," "a first fabric," or "a first foam material," includes, but is not limited to, two or more such phase change materials, first fabrics, first foam materials, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of “about 0.1% to 5%” should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms “about,” “approximate,” “at or about,” and “substantially” mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that “about” and “at or about” mean the nominal value indicated ±10% variation unless otherwise indicated or inferred. In general, an amount, size, formulation, parameter or other quantity or characteristic is “about,” “approximate,” or “at or about” whether or not expressly stated to be such. It is understood that where “about,” “approximate,” or “at or about” is used before a quantitative value, the parameter also includes the specific quantitative value itself, unless specifically stated otherwise.

As used herein, the term “effective amount” refers to an amount that is sufficient to achieve the desired modification of a physical property of the composition or material. For example, an “effective amount” of a phase change material refers to an amount that is sufficient to achieve the desired property modulated by the phase change material, e.g. achieving the desired level of cooling while a disclosed sleep mask product is used by a human subject. The specific level in terms of dry weight of phase material per square meter required as an effective amount will depend upon a variety of factors including the amount and type of phase change material, amount and type of fabrics and foams used in the sleep mask product, amount and temperature for phase change of the phase change material.

As used herein, the terms “optional” or “optionally” means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

B. Reference Characters

Like reference characters or numbers refer to like elements, aspects and/or components throughout, and explanations that duplicate one another will be omitted. The following table, Table 1, provides a list of the various reference characters used herein throughout along with a short description of the reference character. Further discussion of use, context, construction, and the like for an element, aspect, or component referred to by a reference character is provided herein below.

TABLE 1

List of Reference Characters Used in Drawings.

Figure 2C:
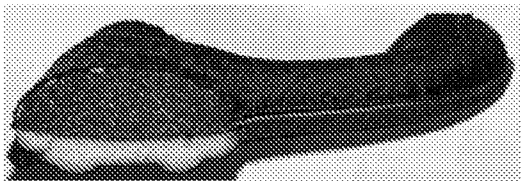
FIGS. 2A-2D show representative depictions of a disclosed sleep mask product.
Figure 2B:
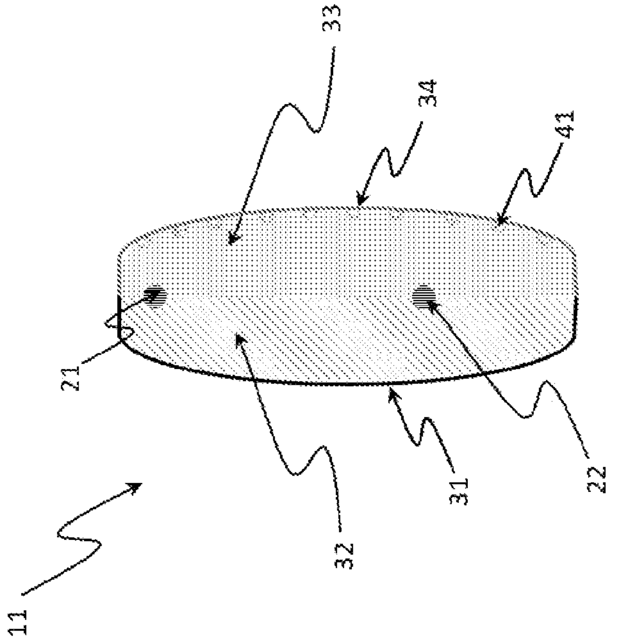
Figure 2A:
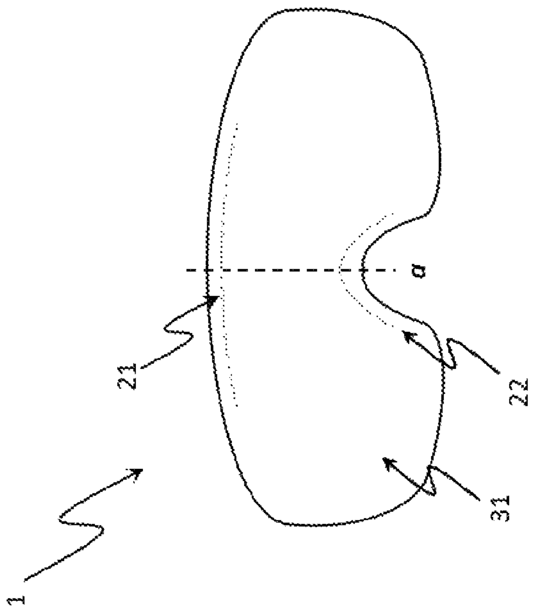
Figure 3C:
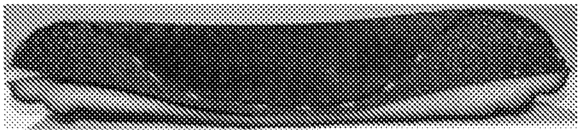
FIGS. 3A-3C show representative depictions of a disclosed sleep mask product.
Figure 3B:
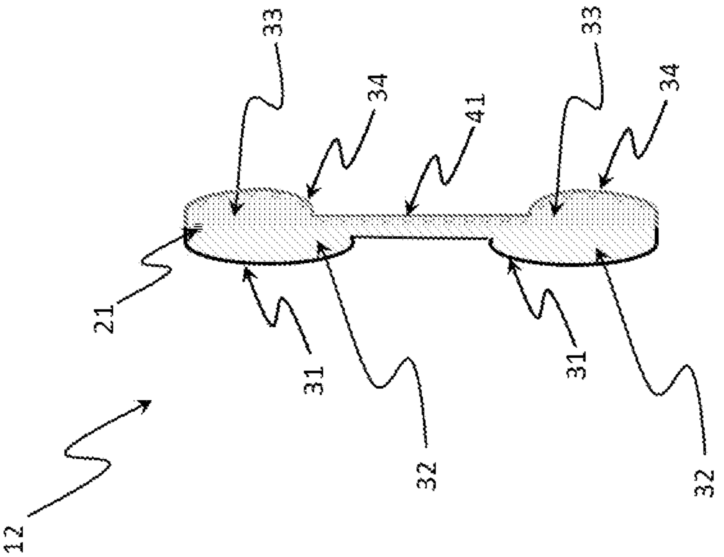
Figure 3A:
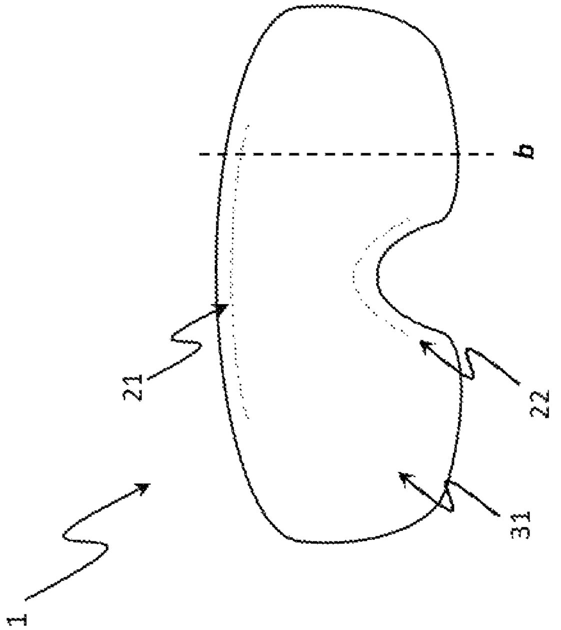

| Reference Character | Description |
|---|---|
| 1 | Front plan view of a representative disclosed sleep mask product (view down onto a first fabric layer). |
| 11 | Cross-sectional view from a representative disclosed sleep mask product at about index position a (as shown in FIG. 2A). |
| 12 | Cross-sectional view from a representative disclosed sleep mask product at about index position b (as shown in FIG. 3A). |
| 14 | Cross-sectional view of a second fabric layer comprising a phase change material in a discontinuous pattern. |
| 15 | Plan view of a second fabric layer comprising a phase change material in a discontinuous pattern. The plan view is of a second surface showing the discountinuous pattern of phase change material thereon. |
| 16 | Plan view of a second fabric layer comprising a phase change material in a discontinuous pattern. The plan view is of a first surface showing with the arrangement of a phase change material thereon on the second surface shown by hatched lines. |
| 21 | Brow fitting component. |
| 22 | Nose fitting component. |
| 31 | First fabric layer. |
| 32 | First foam layer. |
| 33 | Second foam layer. |
| 34 | Second fabric layer comprising a phase change material or composition thereon. |
| 41 | Discontinuous pattern coating comprising a phase change material on an inner surface of a second fabric layer. |

C. Sleep Mask Products

In one aspect, the disclosure relates to sleep mask products comprising a mask body and a mask strap. In various aspects, the mask strap has a first plurality of attachment points to a first lateral edge of the mask body and a second plurality of attachment points to a second lateral edge of the mask body. It is appreciated that an inner surface of the mask body together with an inner surface of the mask strap can form an annulus configured to allow placement of the mask body on a face of a human subject and placement of the mask strap around lateral and anterior portions of a head of the human subject. More specifically, in one aspect, the present disclosure relates to a mask body comprising a first fabric layer; a second fabric layer; a first foam layer; and a second foam layer; such that at least the second fabric layer comprises a phase change material coated thereon, e.g., a distinuous patterned coating or a continuous coating.

In one aspect, the disclosure relates to sleep mask products comprising: a mask body and a mask strap; wherein the mask strap has a first plurality of attachment points to a first lateral edge of the mask body and a second plurality of attachment points to a second lateral edge of the mask body; wherein an inner surface of the mask body together with an inner surface of the mask strap can form an annulus configured to allow placement of the mask body on a face of a human subject and placement of the mask strap around lateral and anterior portions of a head of the human subject; wherein the mask body comprises a first fabric layer; a second fabric layer; a first foam layer; and a second foam layer; wherein the first fabric layer has a first fabric outer surface and a first fabric inner surface; wherein the second fabric layer has a second fabric outer surface and a second fabric inner surface; wherein the first foam layer has a first foam layer first surface and a first foam layer second surface; wherein the second foam layer has a second foam layer first surface and a second foam layer second surface; wherein the first fabric inner surface contacts the first foam layer first surface; wherein the first foam layer second surface contacts the second foam layer first surface; wherein the second fabric inner surface comprises a phase change material thereon; wherein the second foam layer second surface contacts the phase change material, the second fabric inner surface, or a combination thereof; wherein the mask body has a first eye masking area, a second eye masking area, and a nose area; wherein the first eye masking area is configured to cover a first eye of the human subject and mitigate passage of light to the first eye; wherein the second eye masking area is configured to cover a second eye of the human subject and mitigate passage of light to the second eye; wherein the mask body has a mask body upper edge that is configured to be in contact with a portion of the brow or forehead when wore by the human subject; wherein the nose area is configured to fit over a nose of the human subject; wherein a brow fitting component is positioned parallel to the mask body upper edge and between the first foam layer second surface and the second foam layer first surface; and wherein nose fitting component is positioned parallel to the nose area edge and between the first foam layer second surface and the second foam layer first surface.

Temperature controlled phase change material (PCM) is a material that stores or releases a large amount of energy during a change in state or phase, e.g. crystallization (solidifying) or melting (liquefying), at a specific temperature. During such phase changes, the temperature of the material remains relatively constant. Thus, when crystallized PCM is exposed to heat from a human body for example, it continuously absorbs heat and changes from solid to liquid. While the PCM melts, temperature of the PCM remains constant at the melting point until all the material has changed into a liquid.

Thus, an attractive feature of PCM is that when it is set at a specific temperature, it maintains that temperature while absorbing heat until the material has changed from a solid to a liquid. For example, if PCM is initially set at 15° C. and exposed to a human body, it will maintain a constant temperature of 15° C. while absorbing body heat until the material has changed from a solid to a liquid (approximately 3 to 6 hours with some PCM materials). An advantage of PCM is that it is extremely portable, easy to apply, and can work for an extended period with minimal thermal discomfort or obstruction. The PCM may be encapsulated or formulated to allow for easy application to the disclosed second fabric layer, e.g., printing, immersion, and the like. A representative, but non-limiting example, of a commercially available PCM is Backote P1F-220-B and other related PCM materials available from Apexical, Inc. (Spartanburg, South Carolina).

The first fabric layer can be a suitable textile material, e.g., a woven or knit fabric comprising any natural or synthetic material, including but not limited to cotton, linen, microfiber, etc. In a further aspect, the first fabric is a nylon, a polyester, a polyethylene, or blends of any of the foregoing.

The second fabric layer can be a suitable textile material, e.g., a woven or knit fabric comprising any natural or synthetic material, including but not limited to cotton, linen, microfiber, etc. In a further aspect, the second fabric is a nylon, a polyester, a polyethylene, or blends of any of the foregoing. In some aspects, the first fabric layer and the second fabric layer utilize the same or similar fabrics. In other aspects, the first fabric layer and the second fabric layer utilize different fabrics. In a further aspect, the amount of the PCM coating, whether a discontinuous patterned coating or continuous coating, is present in an amount from about 30 grams PCM per square meter second fabric to about 100 grams PCM per square meter second fabric. In a particular, but non-limiting, aspect, the amount of the PCM coating is present in an amount from about 55 grams PCM per square meter second fabric to about 65 grams PCM per square meter second fabric. In a further particular, but non-limiting, aspect, the amount of the PCM coating is present in an amount of about 60 grams PCM per square meter second fabric.

In various aspects, the thickness of a PCM coating, whether a discontinuous patterned coating or continuous coating, is from about 0.05 mm to about 1.5 mm. In a further aspect, the thickness of a PCM coating, whether a discontinuous patterned coating or continuous coating, is between about 0.10 and about 0.25 mm, or between 0.15 mm and about 0.20 mm, such as about 0.18 mm, or between about 0.25 and about 0.40, or between 0.30 and about 0.35 mm, such as about 0.33 mm. In a particular, but non-limiting, aspect, the PCM coating, whether a discontinuous patterned coating or continuous coating, is from about 0.12 mm to about 0.19 mm. In a further particular, but non-limiting, aspect, the PCM coating, whether a discontinuous patterned coating or continuous coating, is from about 0.14 mm to about 0.18 mm. In a still further particular, but non-limiting, aspect, the PCM coating, whether a discontinuous patterned coating or continuous coating, is from about 0.15 mm to about 0.175 mm. In a yet further particular, but non-limiting, aspect, the PCM coating, whether a discontinuous patterned coating or continuous coating, is from about 0.155 mm to about 0.165 mm. In an even further particular, but non-limiting, aspect, the PCM coating, whether a discontinuous patterned coating or continuous coating, is from about 0.158 mm to about 0.162 mm.

In various aspects, the PCM material can further comprise one or more additive, e.g., suitable binders, adhesives, flow agents, reflective materials, a polymer latex binder, and including a surfactant, a dispersant, an antifoam agent, a thickener, and the like in order to optimize manufacturability or add additional properties to a coating layer. In some aspects, the one or more additive are removed by evaporation, sublimation, or combinations thereof, following application of the coating to a fabric layer.

In a further aspect, the PCM material has a desired phase change or melting point, e.g., inclusive of any available or customized melting point such as 20° C., 21° C., 22° C., 23° C., 24° C., 25° C., 26° C., 27° C., 28° C., 29° C., 30° C., 31° C. 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C.; or a range have a lower and upper bound from any of the foregoing temperatures. In a still further aspect, the PCM coating comprises a first PCM material and a second PCM material wherein the first PCM material and the second PCM material have different phase change temperatures. For example, the first PCM material and the second PCM material can have phase change temperatures that differ by about 1° C. to about 30° C.

The PCM material utilized can be any form allowing for coating as described herein, e.g., a microencapsulated phase change material (PCM) in any form such as but not limited to a slurry, wet cake, and/or dry powder or combinations thereof.

In various aspects, a disclosed sleep mask product has a latent heat capacity of greater than about 2.5 J/g, greater than about 3.0 J/g, greater than about 3.5 J/g, greater than about 4.0 J/g, greater than about 4.5 J/g, greater than about 5.0 J/g, greater than about 5.5 J/g, greater than about 6.0 J/g, greater than about 6.5 J/g, greater than about 7.0 J/g, greater than about 7.5 J/g, greater than about 8.0 J/g, greater than about 8.5 J/g, greater than about 9.0 J/g, greater than about 9.5 J/g, and greater than about 10.0 J/g. It is understood that the latent heat capacity is determined using differential scanning calorimetry in a method based on or in accordance with DIN EN 16806-1. In a further aspect, a disclosed sleep mask product has a latent capacity that is a range of the foregoing values, e.g., a disclosed sleep mask product has a latent capacity of from about 2.5 J/g to about 10.0 J/g, from about 3.0 J/g to about 10.0 J/g, from about 3.5 J/g to about 10.0 J/g, from about 4.0 J/g to about 10.0 J/g, from about 4.5 J/g to about 10.0 J/g, from about 5.0 J/g to about 10.0 J/g, from about 5.5 J/g to about 10.0 J/g, from about 6.0 J/g to about 10.0 J/g, from about 6.5 J/g to about 10.0 J/g, from about 7.0 J/g to about 10.0 J/g, from about 7.5 J/g to about 10.0 J/g, and the like.

In various aspects, the phase change coating may be continuous or a discontinuous patterned coating. If the phase change coating is a discontinuous patterned coating it can be regular and repeating or random. “Continuous” as used herein means that from one edge of the fabric to the other edge there is a path that contains the patterned coating and that at least some of the patterned coating areas are connected. “Discontinuous” as used herein means that the patterned coated areas are discontinuous and not touching one another. In a discontinuous patterned coating, there is no path from one edge of the fabric to the other that contains the patterned coating. Regular or repeating patterns mean that the pattern has a repeating structure to it, e.g., as depicted in FIGS. 4A-4F. A random pattern is a discontinuous coating such there is essentially no repeat to the discontinuous patterned coating.

Figure 4B:
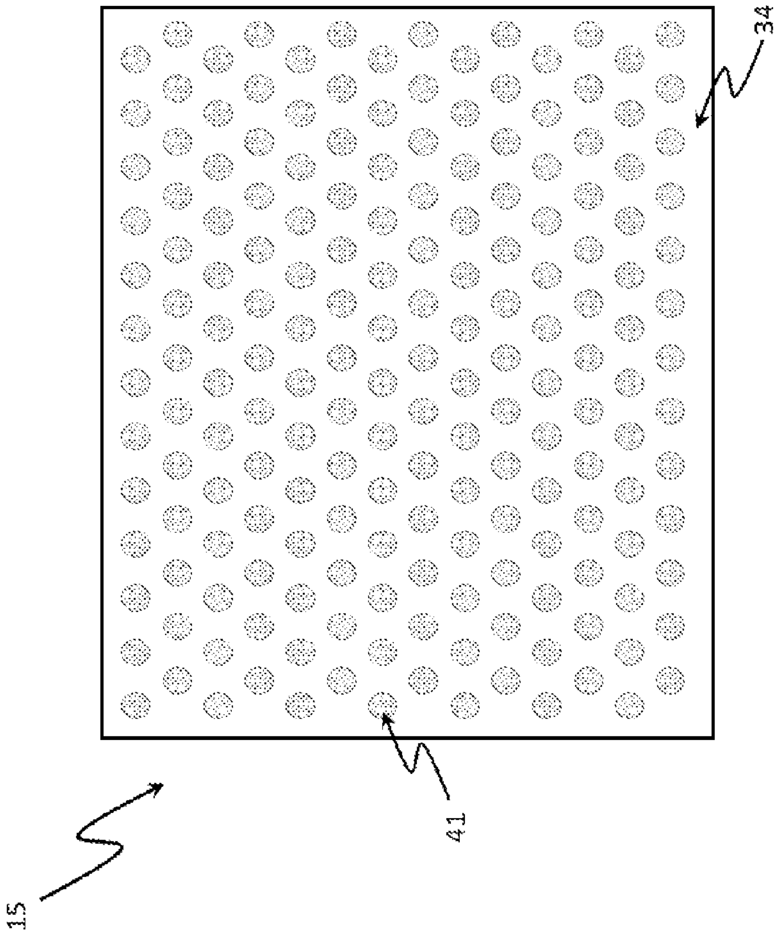
FIGS. 4A-4F show representative depictions of a second fabric layer with a phase change coating.
Figure 4A:
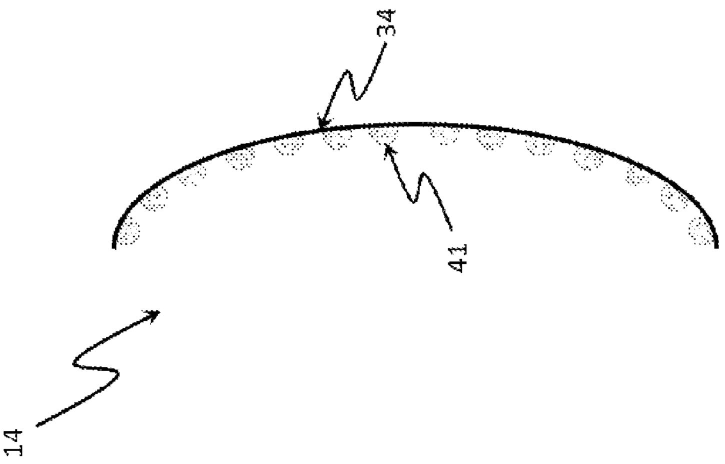
Figure 4E:
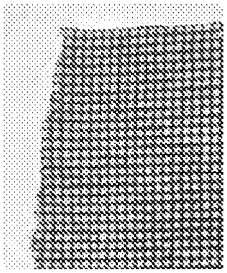
Figure 4D:
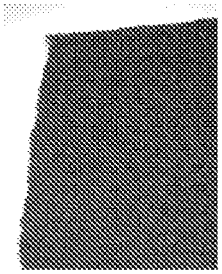
Figure 4F:
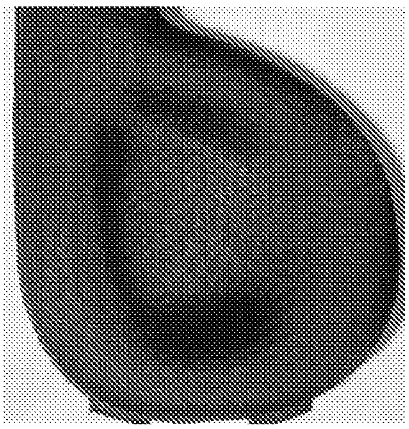
Figure 4C:
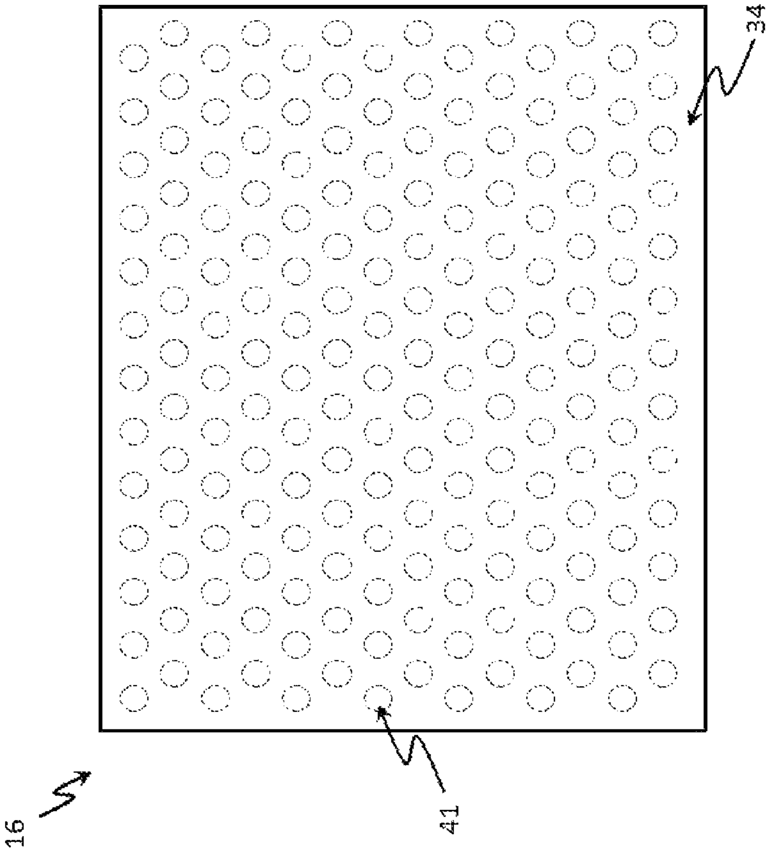
Figure 5:
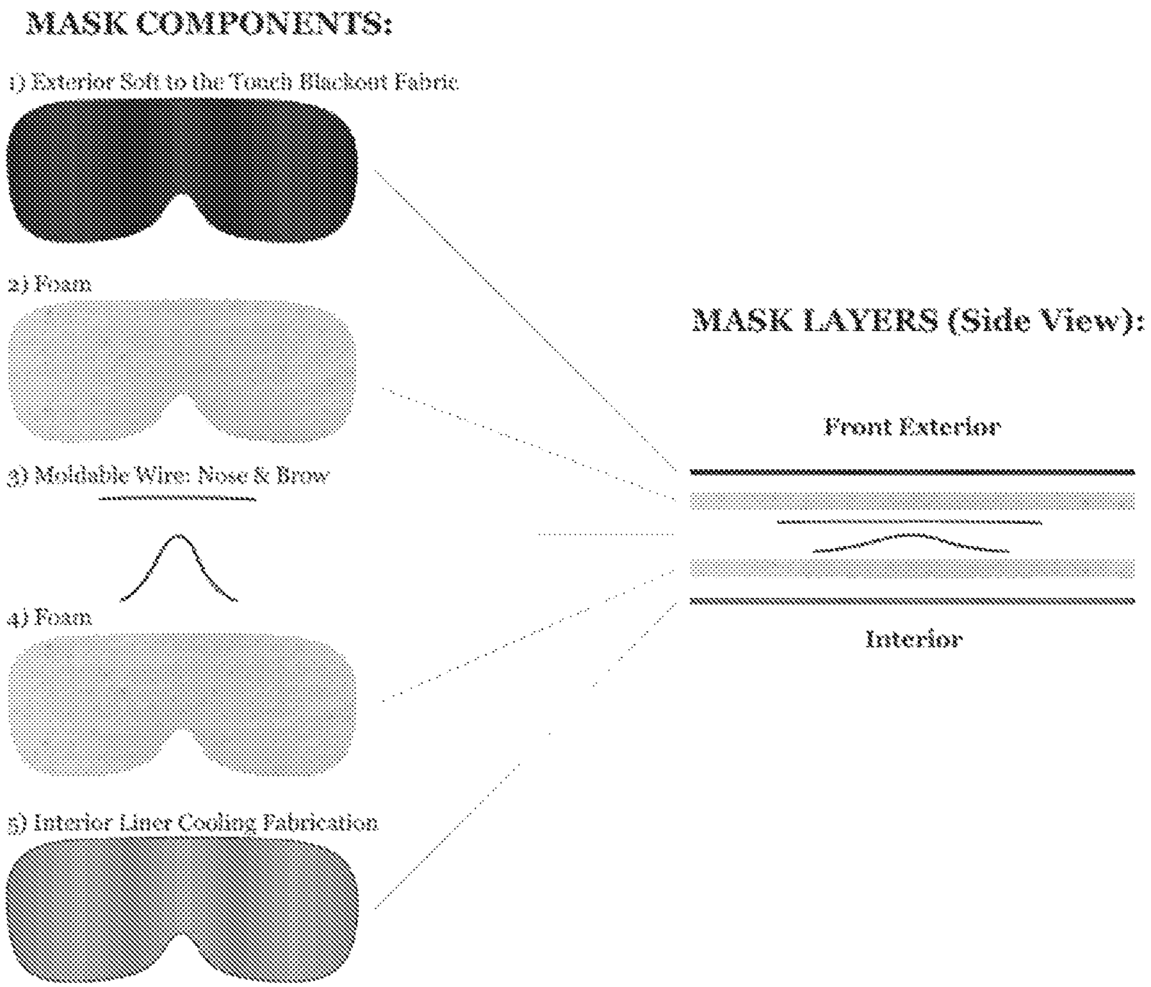
FIG. 5 shows a schematic representation of the disclosed fabric and foam layers, with the brow and nose fitting components, and the relative arrangement of each in a cross-sectional side view.
Figure 6:
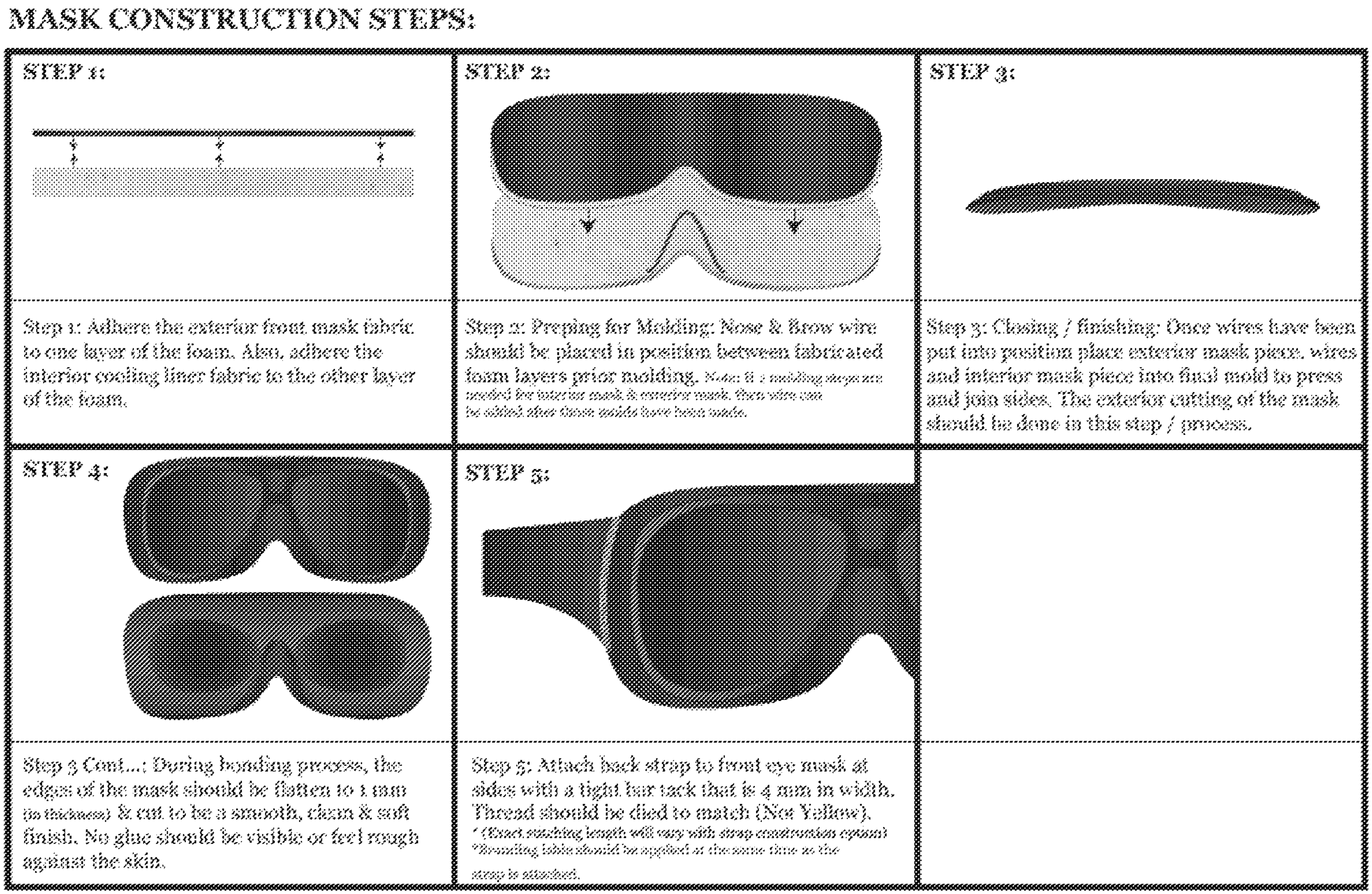
FIG. 6 shows a representative disclosed method of fabricating a disclosed sleep mask product.
Figure 7A:
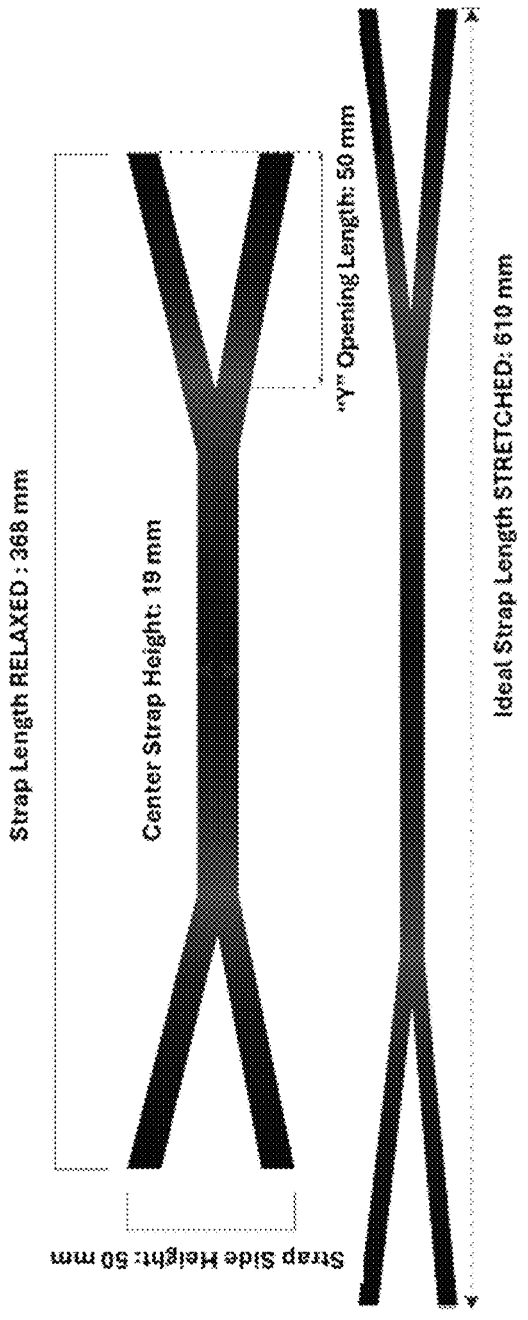
FIGS. 7A-7B show representative schematic depictions of a disclosed sleep mask strap.
Figure 7B:
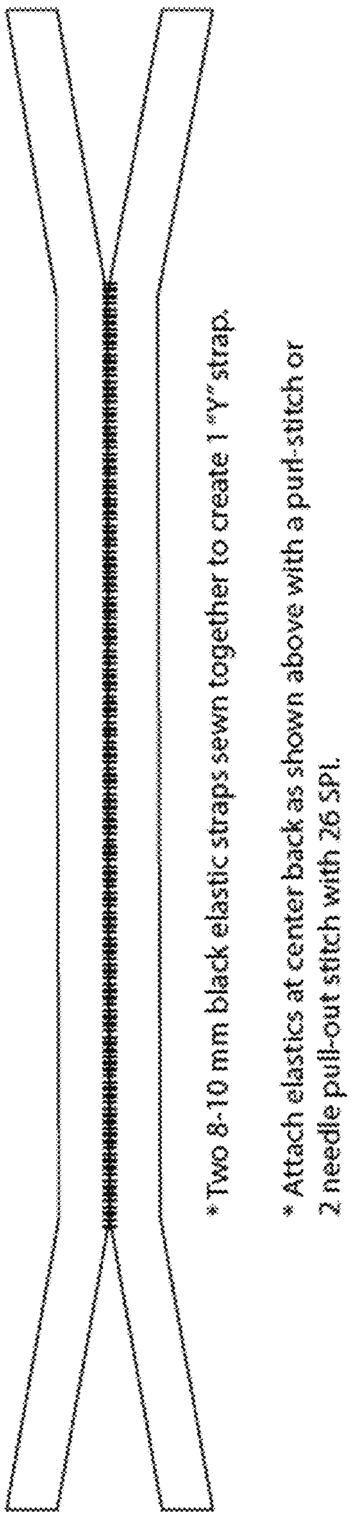

FIGS. 4A-4F show representative depictions of a second fabric layer with a phase change coating. FIG. 4A shows a representative cross-sectional side view of a second fabric layer having thereon a phase change coating on a second fabric inner surface such that the phase change coating is a discontinuous patterned coating. FIG. 4B shows a representative plan view of a second fabric layer inner surface having a phase change coating thereon such that the phase change coating forms a discontinuous patterned coating having a regular pattern. FIG. 4C shows a representative plan view of a second fabric layer outer surface having a phase change coating on the second fabric inner surface such that the phase change coating forms a discontinuous patterned coating having a regular pattern. FIG. 4D shows a photographic image of a representative plan view of a second fabric layer outer surface similar in context to the drawing of FIG. 4C. FIG. 4E shows a photographic image of a representative plan view of a second fabric layer inner surface similar in context to the drawing of FIG. 4B. It should be noted that photographic images shown in FIGS. 4D-4E are of a second fabric layer before fabrication into a disclosed sleep mask product. FIG. 4F shows a photographic image of a representative plan view of a second fabric layer inner surface fabricated as part of a disclosed sleep mask product. The photographic image is of the region corresponding to a first eye area and a portion of the nose area.

As mentioned above, FIGS. 4B-4C depict an aspect where the discontinuous patterned coating is in a dot pattern. This pattern is discontinuous and repeating. The dots may be equally spaced on the fabric or may have differing densities of dots or sizing of dots across the surface of the fabric. A dot pattern may be preferred for improved resistance to breaking under mechanical pressure.

A discontinuous patterned coated layer may be formed by any known method of forming a patterned coating including but not limited to screen printing, inkjet printing, gravure printing, patterned printing, thermal transfer, spray coating, and silk printing. Screen printing can be preferred because is simple, cheap, common, versatile in terms of add-on, pattern. It is also mild to microencapsulated PCM particles, if that is the form or formulation of the PCM material used for coating.

The thickness and/or physical composition of the discontinuous patterned coating may vary over the length and/or width of the fabric layer coated. For example, it may be preferred in some aspects to have a thicker coating or more densely packed pattern in some areas of a fabric layer such as peripheral portions of the sleep mask body that will be in direct contact with skin when the sleep mask product is used by a human subject.

In one aspect, a discontinuous patterned coating covers between about 5 and 95% of the surface area of the fabric layer coated. In other aspects, the discontinuous patterned coating may cover between about 5 and 70%, 10 and 60%, 45 and 90%, 45 and 75%, greater than 15%, greater than 20% and greater than 30% of the surface area of the fabric layer coated.

The brow fitting component and the nose fitting component can be any material wire having minimum elasticity and capable of being deformed by hand to change its shape to allow repeated conforming to the contours of target areas for fit such as the brow or nose, e.g., a malleable wire. In some aspects, the brow fitting component and the nose fitting component are made from essentially the same material, e.g., the same type of malleable wire. In other aspects, the brow fitting component and the nose fitting component are made from essentially different materials. In a still further aspect, the cross-sectional diameter or thickness of the brow fitting component and the nose fitting component can be substantially the same. In still other aspects, the cross-sectional diameter or thickness of the brow fitting component and the nose fitting component can be different.

In a yet further aspect, the malleable wire can be made from various forms of metal, e.g. aluminum, copper, nickel, or other metal alloys. The malleable wire can be plastic-coated, e.g., to thermally insulate and/or to improve durability.

The malleable wire retains such changed shape until again deformed by hand. The malleable wire is of such length and general configuration as to fit within and conform to and generally define an outer periphery of the annular configuration of the sleeve throughout most of the length of that periphery. An elastic connector is attached to each of the respective ends of the tubular sleeve to elastically interconnect the ends to complete the annulus in such a way that the elastic stretch is provided and the inner periphery of the annulus will serve as a hat band adjusting to the wearer's head size. The ends of the wire may be flattened, rounded and bent slightly outwardly to prevent penetration of fabric and to avoid the possibility that in any position where the wire approaches the head of the wearer it might tend to dig into the head.

Turning now to FIGS. 2A-2C which show representative depictions of a disclosed sleep mask product. FIG. 2A shows a front plan view of a representative sleep mask product with positioning of a brow fitting component and a nose fitting, with index line a shown marking the position of the cross-sectional view depicted FIG. 2B. FIG. 2B shows a cross-sectional view taken at the position of the index line shown in FIG. 2A. FIG. 2C shows a photographic image of a cross-sectional portion of a disclosed sleep mask at a position similar to that shown in the drawing of FIG. 2B. All reference characters have the meaning as given in Table 1 herein above.

Figure 2D:
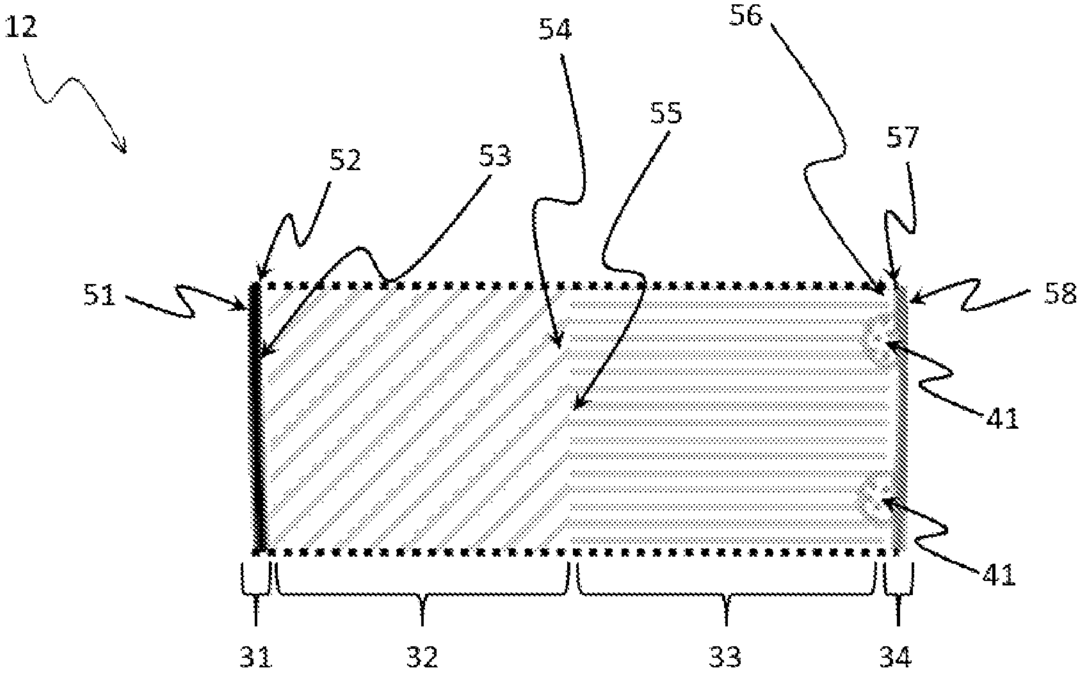

As shown in FIG. 2A, a representative disclosed sleep mask product 1 has a first and a second eye area that can align over the eyes of a human subject using the sleep mask product. Moreover, the representative disclosed sleep mask product 1 as a nose area that is configured so as to fit over a nose. The relative locations of the brow fitting component 21 and nose fitting component 22 are shown as dashed lines since they are positioned beneath the outer or front surface of a sleep mask product. This is more clearly depicted in the cross-sectional view 12 depicted in FIG. 2B which also shows the arrangement or relative positioning of the first fabric layer 31, the first foam layer 32, the second foam layer 33, and the second fabric layer 34 comprising a discontinuous pattern coating comprising a phase change material 41. As noted above, FIG. 2B is a cross-sectional view from index line a as shown in FIG. 2A. FIG. 2B shows a portion of the view highlighted with dashed line box 12. This portion of the cross-sectional view is shown in detail in FIG. 2D in order to delineate the relation of the following features:

The first fabric layer 31, the first foam layer 32, the second foam layer 33, and the second fabric layer 34;

The first fabric layer 31 has a first fabric layer outer surface 51 and a first fabric layer inner surface 52;

The first foam layer 32 has a first foam layer outer surface 53 and a first foam layer inner surface 54;

The second foam layer 33 has a second foam layer inner surface 55 and a second foam layer outer surface 56;

The second fabric layer 34 has a second fabric layer inner surface 57 and a second fabric layer outer surface 58;

The first fabric layer inner surface 52 is proximal to and/or in contact with the first foam layer outer surface 53;

The first foam layer inner surface 54 is proximal to and/or in contact with the second foam layer inner surface 55; and The second foam layer outer surface 56 is proximal to and/or in contact with the second fabric layer inner surface 55.

In various aspects, the first fabric layer is in contact and thermally bonded to the first foam layer. In a further aspect, the first foam layer is in contact and thermally bonded to the second foam layer. In a yet further aspect, the second foam layer is in contact and thermally bonded to the second fabric layer. It is understood that in various aspects the contact and thermal bonding can occur throughout the given layers, or at least in part of the given layers. In some aspects, the edge or periphery of the sleep mask product comprises a weld that provides, at least in part, a thermal bond between various fabric and foam layers. In a further aspect, the weld as a width from about 0.1 mm to about 1.0 mm from the outer edge to the inner edge of the weld. In a still further aspect, the weld as a width from about 0.2 mm to about 0.8 mm from the outer edge to the inner edge of the weld. In a yet further aspect, the weld as a width from about 0.3 mm to about 0.7 mm from the outer edge to the inner edge of the weld. In an even further aspect, the weld as a width of about 0.5 mm from the outer edge to the inner edge of the weld.

FIGS. 3A-3C show representative depictions of a disclosed sleep mask product. FIG. 3A shows a front plan view of a representative sleep mask product with positioning of a brow fitting component and a nose fitting, with index line b shown marking the position of the cross-sectional view depicted FIG. 3B. FIG. 3B shows a cross-sectional view taken at the position of the index line shown in FIG. 3A. FIG. 3C shows a photographic image of a cross-sectional portion of a disclosed sleep mask at a position similar to that shown in the drawing of FIG. 3B. All reference characters have the meaning as given in Table 1 herein below.

As shown in FIG. 3A, a representative disclosed sleep mask product 1 has a first and a second eye area that can align over the eyes of a human subject using the sleep mask product. Moreover, the representative disclosed sleep mask product 1 as a nose area that is configured so as to fit over a nose. The relative locations of the brow fitting component 21 and nose fitting component 22 are shown as dashed lines since they are positioned beneath the outer or front surface of a sleep mask product. This is more clearly depicted in the cross-sectional view 12 depicted in FIG. 3B which also shows the arrangement or relative positioning of the first fabric layer 31, the first foam layer 32, the second foam layer 33, and the second fabric layer 34 comprising a discontinuous pattern coating comprising a phase change material 41. As noted above, FIG. 3B is a cross-sectional view from index line b as shown in FIG. 3A. FIGS. 3B-3C show that the outer portions of the cross-section are thicker such that the central portion is relatively thin by comparison and forms a cavity. This configuration permits air space and distance for the portion directly over an eye to facilitate enhanced comfort for the human subject using the sleep mask product. In contrast, the cross-sectional area from the central nose region can be of more uniform thickness.

In various aspects, the disclosed sleep mask product is made using compression molding methods, e.g., compression molding of the first foam layer and the second foam layer, either independently compression mold and then assembled or alternatively, compression molded together. In a further aspect, compression molding can be carried out at temperatures and pressures suitable to the materials used in the first foam layer and second foam layer. For example, in some aspects, compression molding is carried out at a temperature from about 125° C. to about 130° C. under a pressure of from about 4 bar to about 6 bar for a time from about 5 minutes to about 7 minutes.

D. Aspects

The following listing of exemplary aspects supports and is supported by the disclosure provided herein.

Aspect 1. A sleep mask product comprising: a mask body and a mask strap; wherein the mask strap has a first attachment point to a first lateral edge of the mask body and a second attachment point to a second lateral edge of the mask body; wherein an inner surface of the mask body together with an inner surface of the mask strap forms an annulus configured to allow placement of the mask body on a face of a human subject and placement of the mask strap around lateral and anterior portions of a head of the human subject; wherein the mask body comprises a first fabric layer; a second fabric layer; a first foam layer; and a second foam layer; wherein the first fabric layer has a first fabric outer surface and a first fabric inner surface; wherein the second fabric layer has a second fabric outer surface and a second fabric inner surface; wherein the first foam layer has a first foam layer first surface and a first foam layer second surface; wherein the second foam layer has a second foam layer first surface and a second foam layer second surface; wherein the first fabric inner surface contacts the first foam layer first surface; wherein the first foam layer second surface contacts the second foam layer first surface; wherein the second fabric inner surface comprises a phase change material thereon; wherein the second foam layer second surface contacts the phase change material, the second fabric inner surface, or a combination thereof; wherein the mask body has a first eye masking area, a second eye masking area, and a nose area; wherein the first eye masking area is configured to cover a first eye of the human subject and mitigate passage of light to the first eye; wherein the second eye masking area is configured to cover a second eye of the human subject and mitigate passage of light to the second eye; wherein the mask body has a mask body upper edge that is configured to be in contact with a portion of the brow or forehead when wore by the human subject; wherein the nose area is configured to fit over a nose of the human subject; wherein a brow fitting component is positioned parallel to the mask body upper edge and between the first foam layer second surface and the second foam layer first surface; and wherein nose fitting component is positioned parallel to the nose area edge and between the first foam layer second surface and the second foam layer first surface.

Aspect 2. The sleep mask product of Aspect 1, wherein the phase change material is printed on the second fabric layer inner surface.

Aspect 3. The sleep mask product of Aspect 1 or Aspect 2, wherein the phase change material forms a phase change coating on the second fabric layer inner surface.

Aspect 4. The sleep mask product of Aspect 3, wherein the phase change coating forms a discontinuous patterned coating on the second fabric layer inner surface.

Aspect 5. The sleep mask product of Aspect 4, wherein the discontinuous patterned coating is a regular or repeating discontinuous pattern.

Aspect 6. The sleep mask product of Aspect 4, wherein the discontinuous patterned coating is a randomly distributed discontinuous pattern.

Aspect 7. The sleep mask product of Aspect 3, wherein the phase change coating forms a continuous coating on the second fabric layer inner surface.

Aspect 8. The sleep mask product of any one of Aspect 1-Aspect 7, wherein the phase change coating is present on the second fabric layer inner surface in an amount of from about 25 grams dry weight per square meter to about 100 grams dry weigh per square meter.

Aspect 9. The sleep mask product of Aspect 8, wherein the phase change coating is present on the second fabric layer inner surface in an amount of from about 30 grams dry weight per square meter to about 90 grams dry weigh per square meter.

Aspect 10. The sleep mask product of Aspect 8, wherein the phase change coating is present on the second fabric layer inner surface in an amount of from about 40 grams dry weight per square meter to about 80 grams dry weigh per square meter.

Aspect 11. The sleep mask product of Aspect 8, wherein the phase change coating is present on the second fabric layer inner surface in an amount of from about 50 grams dry weight per square meter to about 70 grams dry weigh per square meter.

Aspect 12. The sleep mask product of Aspect 8, wherein the phase change coating is present on the second fabric layer inner surface in an amount of from about 55 grams dry weight per square meter to about 65 grams dry weigh per square meter.

Aspect 13. The sleep mask product of any one of Aspect 1-Aspect 12, wherein the first foam layer comprises a mixture of open cell foam material, closed cell foam material, and/or semi-closed cell foam material.

Aspect 14. The sleep mask product of any one of Aspect 1-Aspect 12, wherein the first foam layer comprises at least one region having an open cell foam material, closed cell foam material, or semi-closed cell foam material and at least one other region comprising a different cell foam material.

Aspect 15. The sleep mask of Aspect 14, wherein a different cell foam material is a material having a different cell structure.

Aspect 16. The sleep mask of Aspect 14, wherein a different cell foam material is a material having a different density.

Aspect 17. The sleep mask product of any one of Aspect 1-Aspect 12, wherein the first foam layer is a semi-closed cell foam material.

Aspect 18. The sleep mask product of any one of Aspect 1-Aspect 12, wherein the first foam layer is an open cell foam material.

Aspect 19. The sleep mask product of any one of Aspect 1-Aspect 12, wherein the first foam layer is a closed cell foam material.

Aspect 20. The sleep mask product of any one of Aspect 13-Aspect 19, wherein the first foam layer comprises a polyurethane foam material.

Aspect 21. The sleep mask product of any one of Aspect 13-Aspect 20, wherein the first foam layer is a high-density foam material.

Aspect 22. The sleep mask product of Aspect 21, wherein the first foam layer has a density of greater than or equal to about 1.5 $lbs/ft^3$.

Aspect 23. The sleep mask product of Aspect 21, wherein the first foam layer has a density of greater than or equal to about 1.6 $lbs/ft^3$.

Aspect 24. The sleep mask product of Aspect 21, wherein the first foam layer has a density of greater than or equal to about 1.7 $lbs/ft^3$.

Aspect 25. The sleep mask product of Aspect 21, wherein the first foam layer has a density of greater than or equal to about 1.8 $lbs/ft^3$.

Aspect 26. The sleep mask product of Aspect 21, wherein the first foam layer has a density of greater than or equal to about 1.9 $lbs/ft^3$.

Aspect 27. The sleep mask product of Aspect 21, wherein the first foam layer has a density of greater than or equal to about 2.0 $lbs/ft^3$.

Aspect 28. The sleep mask product of any one of Aspect 1-Aspect 27, wherein the second foam layer comprises a mixture of open cell foam material, closed cell foam material, and/or semi-closed cell foam material.

Aspect 29. The sleep mask product of any one of Aspect 1-Aspect 27, wherein the second foam layer comprises at least one region having an open cell foam material, closed cell foam material, or semi-closed cell foam material and at least one other region comprising a different cell foam material.

Aspect 30. The sleep mask product of Aspect 29, wherein a different cell foam material is a material having a different cell structure.

Aspect 31. The sleep mask product of Aspect 29, wherein a different cell foam material is a material having a different density.

Aspect 32. The sleep mask product of any one of Aspect 1-Aspect 27, wherein the second foam layer is a semi-closed cell foam material.

Aspect 33. The sleep mask product of any one of Aspect 1-Aspect 27, wherein the second foam layer is an open cell foam material.

Aspect 34. The sleep mask product of any one of Aspect 1-Aspect 27, wherein the second foam layer is a closed cell foam material.

Aspect 35. The sleep mask product of any one of Aspect 28-Aspect 34, wherein the second foam layer is a polyurethane foam material.

Aspect 36. The sleep mask product of any one of Aspect 28-Aspect 35, wherein the second foam layer is a high-density foam material.

Aspect 37. The sleep mask product of Aspect 36, wherein the first foam layer has a density of greater than or equal to about 1.5 $lbs/ft^3$.

Aspect 38. The sleep mask product of Aspect 36, wherein the first foam layer has a density of greater than or equal to about 1.6 $lbs/ft^3$.

Aspect 39. The sleep mask product of Aspect 36, wherein the first foam layer has a density of greater than or equal to about 1.7 $lbs/ft^3$.

Aspect 40. The sleep mask product of Aspect 36, wherein the first foam layer has a density of greater than or equal to about 1.8 $lbs/ft^3$.

Aspect 41. The sleep mask product of Aspect 36, wherein the first foam layer has a density of greater than or equal to about 1.9 $lbs/ft^3$.

Aspect 42. The sleep mask product of Aspect 36, wherein the first foam layer has a density of greater than or equal to about 2.0 $lbs/ft^3$.

Aspect 43. The sleep mask product of any one of Aspect 1-Aspect 42, wherein the first fabric outer surface comprises a decorative image thereon.

Aspect 44. The sleep mask product of Aspect 43, wherein the decorative image is printed on the first fabric outer surface.

Aspect 45. The sleep mask product of Aspect 43, wherein the decorative image is embossed on the first fabric outer surface.

Aspect 46. The sleep mask product of Aspect 44, wherein the decorative image is embroidered on the first fabric outer surface.

Aspect 47. The sleep mask product of Aspect 44, wherein the decorative image is an applique applied to the first fabric outer surface.

Aspect 48. The sleep mask product of any one of Aspect 1-Aspect 47, wherein the brow fitting component comprises a material that is capable of being deformed by hand to change its shape and retaining such changed shape until again deformed by hand; and wherein the brow fitting component is of such length and configuration as to conform to a portion of the brow or forehead and generally define an outer periphery of the mask body positioned proximal to or over the brow, eyebrows, or forehead of the human subject.

Aspect 49. The sleep mask product of Aspect 48, wherein the brow fitting component is a malleable wire.

Aspect 50. The sleep mask product of Aspect 49, wherein the brow fitting component comprises copper, aluminum, steel, brass, or combinations thereof.

Aspect 51. The sleep mask product of Aspect 50, wherein the brow fitting component comprises a copper wire.

Aspect 52. The sleep mask product of any one of Aspect 1-Aspect 51, wherein the nose fitting component comprises a material that is capable of being deformed by hand to change its shape and retaining such changed shape until again deformed by hand; and wherein the nose fitting component is of such length and configuration as to conform to a portion of the nose and generally define an outer periphery of the nose area positioned proximal to or over the nose of the human subject.

Aspect 53. The sleep mask of Aspect 52, wherein the nose fitting component is a malleable wire.

Aspect 54. The sleep mask product of Aspect 53, wherein the nose fitting component comprises copper, aluminum, steel, brass, or combinations thereof.

Aspect 55. The sleep mask product of Aspect 54, wherein the nose fitting component comprises a copper wire.

Aspect 56. The sleep mask product of any one of Aspect 1-Aspect 55, wherein the mask strap comprises an elastic fabric or textile material.

Aspect 57. The sleep mask product of any one of Aspect 1-Aspect 56, wherein the mask strap is attached to the first attachment point and to the second attachment point by stitching, an adhesive, a thermal weld, or combinations thereof.

Aspect 58. The sleep mask product of any one of Aspect 1-Aspect 57, wherein the first fabric has a first fabric outer edge defining the periphery of the first fabric; wherein the second fabric has a second fabric outer edge defining the periphery of the second fabric; and wherein the first fabric outer edge and the second fabric outer edge are joined to one another.

Aspect 59. The sleep mask product of Aspect 58, wherein the first fabric outer edge and the second fabric outer edge are joined to one another by stitching, an adhesive, a thermal weld, or combinations thereof.

Aspect 60. The sleep mask product of any one of Aspect 1-Aspect 59, further comprising an adhesive, a thermal weld, or combinations at contacts of the first fabric inner surface with the first foam layer first surface.

Aspect 61. The sleep mask product of any one of Aspect 1-Aspect 60, further comprising an adhesive, a thermal weld, or combinations at contacts of the first foam layer second surface with the second foam layer first surface.

Aspect 62. The sleep mask product of any one of Aspect 1-Aspect 61, further comprising an adhesive, a thermal weld, or combinations at contacts of the second foam layer second surface with the phase change material, the second fabric inner surface, or a combination thereof.

Aspect 63. The sleep mask product of any one of Aspect 1-Aspect 62, wherein the sleep mask product has a latent heat capacity of greater than about 2.5 J/g when in accordance with DIN EN 16806-1.

Aspect 64. The sleep mask product of any one of Aspect 1-Aspect 62, wherein the sleep mask product has a latent heat capacity of from about 7.0 J/g to about 10.0 J/g, when in accordance with DIN EN 16806-1.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

E. Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Differential Scanning calorimeter Testing and Analysis of Disclosed Sleep Mask. A sleep mask was fabricated as shown in FIGS. 1A-1D, 2C, 3C, and 4D-4F. Two sleep masks were fabricated as disclosed herein (the test masks, "Masks 1+2"), and two sleep masks of a second sleep mask type were fabricated in all respects identical to the test mask except that it did not comprise any phase change material (the control masks, "Masks 3+4"). The test masks and control masks were subjected to Differential Scanning calorimeter ("DSC") testing and analysis in a test method is based on DIN EN 16806-1. Briefly, DSC measurements were performed on a Perkin Elmer instrument and latent heat of fusion (J/g) data generally reported from exothermic (crystallization) peak. The DSC testing procedure utilizes test samples prepared in Perkin Elmer hermitically sealed aluminum sample pans. Testing was preformed under constant N2 flow. Test parameters consist of:

(1) Cooling to −10° C.
(2) Isothermal holding for one minute then,
(3) Heating from −10° C. to 50° C. at 5° C./min.,
(4) Isothermal hold for one minute at 50° C.,
(5) Cooling from 50° C. to −10° C. at 5° C./min.

Data obtained from DSC testing are shown in FIG. 8A (for the test masks, "Masks 1+2") and 8B (for the control masks, "Masks 3+4"). The data were used to determine that the test masks had a latent heat capacity of 9.5 J/g. In contrast, the latent heat capacity of the control masks was essentially nil. Based on the latent heat capacity of a exemplary disclosed sleep mask, the disclosed masks are demonstrated to be capable of robust thermoregulation when used by an end-user.

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A sleep mask product comprising: a mask body and a mask strap;

wherein the mask strap has a first attachment point to a first lateral edge of the mask body and a second attachment point to a second lateral edge of the mask body;

wherein an inner surface of the mask body together with an inner surface of the mask strap forms an annulus configured to allow placement of the mask body on a face of a human subject and placement of the mask strap around lateral and anterior portions of a head of the human subject;

wherein the mask body comprises a first fabric layer; a second fabric layer; a first foam layer; and a second foam layer;

wherein the first fabric layer has a first fabric outer surface and a first fabric inner surface;

wherein the second fabric layer has a second fabric outer surface and a second fabric inner surface;

wherein the first foam layer has a first foam layer first surface and a first foam layer second surface;

wherein the second foam layer has a second foam layer first surface and a second foam layer second surface;

wherein the first fabric inner surface contacts the first foam layer first surface;

wherein the first foam layer second surface contacts the second foam layer first surface;

wherein the second fabric inner surface comprises a phase change material thereon;

wherein the second foam layer second surface contacts the phase change material, the second fabric inner surface, or a combination thereof;

wherein the mask body has a first eye masking area, a second eye masking area, and a nose area;

wherein the first eye masking area is configured to cover a first eye of the human subject and mitigate passage of light to the first eye;

wherein the second eye masking area is configured to cover a second eye of the human subject and mitigate passage of light to the second eye;

wherein the mask body has a mask body upper edge that is configured to be in contact with a portion of the brow or forehead when wore by the human subject;

wherein the nose area is configured to fit over a nose of the human subject;

wherein a brow fitting component is positioned parallel to the mask body upper edge and between the first foam layer second surface and the second foam layer first surface; and wherein nose fitting component is positioned parallel to the nose area edge and between the first foam layer second surface and the second foam layer first surface; wherein the phase change coating is present on the second fabric layer inner surface in an amount of from about 25 grams dry weight per square meter to about 100 grams dry weigh per square meter; wherein the first foam layer is a closed cell foam material and wherein the first foam layer comprises a high-density polyurethane foam material; and wherein the first foam layer has a density of greater than or equal to about 1.5 lbs/ft3.

2. The sleep mask product of claim 1, wherein the phase change material forms a phase change coating on the second fabric layer inner surface.

3. The sleep mask product of claim 2, wherein the phase change coating forms a discontinuous patterned coating on the second fabric layer inner surface.

4. The sleep mask product of claim 1, wherein the first foam layer comprises at least one region having an open cell foam material, closed cell foam material, or semi-closed cell foam material and at least one other region comprising a different cell foam material.

5. The sleep mask product of claim 1, wherein the second foam layer comprises at least one region having an open cell foam material, closed cell foam material, or semi-closed cell foam material and at least one other region comprising a different cell foam material.

6. The sleep mask product of claim 1, wherein the second foam layer is a closed cell foam material.

7. The sleep mask product claim 6, wherein the second foam layer is a high-density polyurethane foam material; and wherein and wherein the first foam layer has a density of greater than or equal to about 1.5 lbs/ft$^3$.

8. The sleep mask product of claim 1, wherein the first fabric outer surface comprises a decorative image thereon.

9. The sleep mask product of claim 8, wherein the decorative image is printed on the first fabric outer surface.

10. The sleep mask product of claim 8, wherein the decorative image is embossed on the first fabric outer surface.

11. The sleep mask product of claim 1, wherein the brow fitting component comprises a material that is capable of being deformed by hand to change its shape and retaining such changed shape until again deformed by hand; and wherein the brow fitting component is of such length and configuration as to conform to a portion of the brow or forehead and generally define an outer periphery of the mask body positioned proximal to or over the brow, eyebrows, or forehead of the human subject.

12. The sleep mask product of claim 11, wherein the brow fitting component is a malleable wire comprising copper, aluminum, steel, brass, or combinations thereof.

13. The sleep mask product of claim 1, wherein the nose fitting component comprises a material that is capable of being deformed by hand to change its shape and retaining such changed shape until again deformed by hand; and wherein the nose fitting component is of such length and configuration as to conform to a portion of the nose and generally define an outer periphery of the nose area positioned proximal to or over the nose of the human subject.

14. The sleep mask of claim 13, wherein the nose fitting component is a malleable wire comprising copper, aluminum, steel, brass, or combinations thereof.

15. The sleep mask product of claim 1, wherein the mask strap is attached to the first attachment point and to the second attachment point by stitching, an adhesive, a thermal weld, or combinations thereof.

16. The sleep mask product of claim 1, wherein the sleep mask product has a latent heat capacity of greater than about 2.5 J/g when in accordance with DIN EN 16806-1.

17. The sleep mask product of claim 16, wherein the sleep mask product has a latent heat capacity of from about 7.0 J/g to about 10.0 J/g, when in accordance with DIN EN 16806-1.

* * * * *